United States Patent [19]

Chu

[11] Patent Number: 5,149,784
[45] Date of Patent: Sep. 22, 1992

[54] PROCESS FOR MAKING VANCOMYCIN

[75] Inventor: Alexander H. T. Chu, Buffalo Grove, Ill.

[73] Assignee: Abbott Laboratories, Abbott Park, Ill.

[21] Appl. No.: 550,424

[22] Filed: Jul. 10, 1990

[51] Int. Cl.$^5$ .............................. C07K 1/14; C07K 9/00
[52] U.S. Cl. .................................... 530/344; 530/317; 530/322
[58] Field of Search ................ 530/317, 344, 322, 323

[56] References Cited

U.S. PATENT DOCUMENTS

| | | | |
|---|---|---|---|
| 3,067,099 | 12/1962 | McCormick et al. | 424/115 |
| 4,440,753 | 4/1984 | McCormick et al. | 424/124 |
| 4,667,024 | 5/1987 | Sitrin et al. | 536/16.9 |
| 4,845,194 | 7/1989 | Glass et al. | 530/344 |

FOREIGN PATENT DOCUMENTS

| | | |
|---|---|---|
| 0241758 | 10/1987 | European Pat. Off. . |
| 0262941 | 4/1988 | European Pat. Off. . |
| 0294990 | 12/1988 | European Pat. Off. . |
| 0303021 | 2/1989 | European Pat. Off. . |
| 0323150 | 7/1989 | European Pat. Off. . |
| 2151234B | 7/1985 | United Kingdom . |

*Primary Examiner*—Y. Christina Chan
*Attorney, Agent, or Firm*—Andreas M. Danckers; Steven F. Weinstock

[57] ABSTRACT

A process for the manufacture of vancomycin which does not require preparation of a phosphate intermediate. The process consists of loading a vancomycin onto a suitable adsorbent and eluting the vancomycin solution therefrom with an ammonium solvent followed by loading the solution onto a second adsorbent and eluting the purified, vancomycin therefrom with a solvent of alcohol and acid. The purified vancomycin is then crystallized by adding a base solution in an amount sufficient to raise the pH of the vancomycin/base solution to a pH of about 9.5 to 10.5 followed by the addition of an organic solvent such as methanol. The crystallized vancomycin is then reslurried in an aqueous solution and then recrystallized by adding a base solution in an amount sufficient to raise the pH to about 9.5 to about 10.5, followed by the addition of an organic solvent such as methanol. The recrystallized vancomycin is dissolved and titrated with hydrochloric acid to a pH of about 3.0 to 3.5. Vancomycin HCl is precipitated from the solution using an organic solvent.

11 Claims, 1 Drawing Sheet

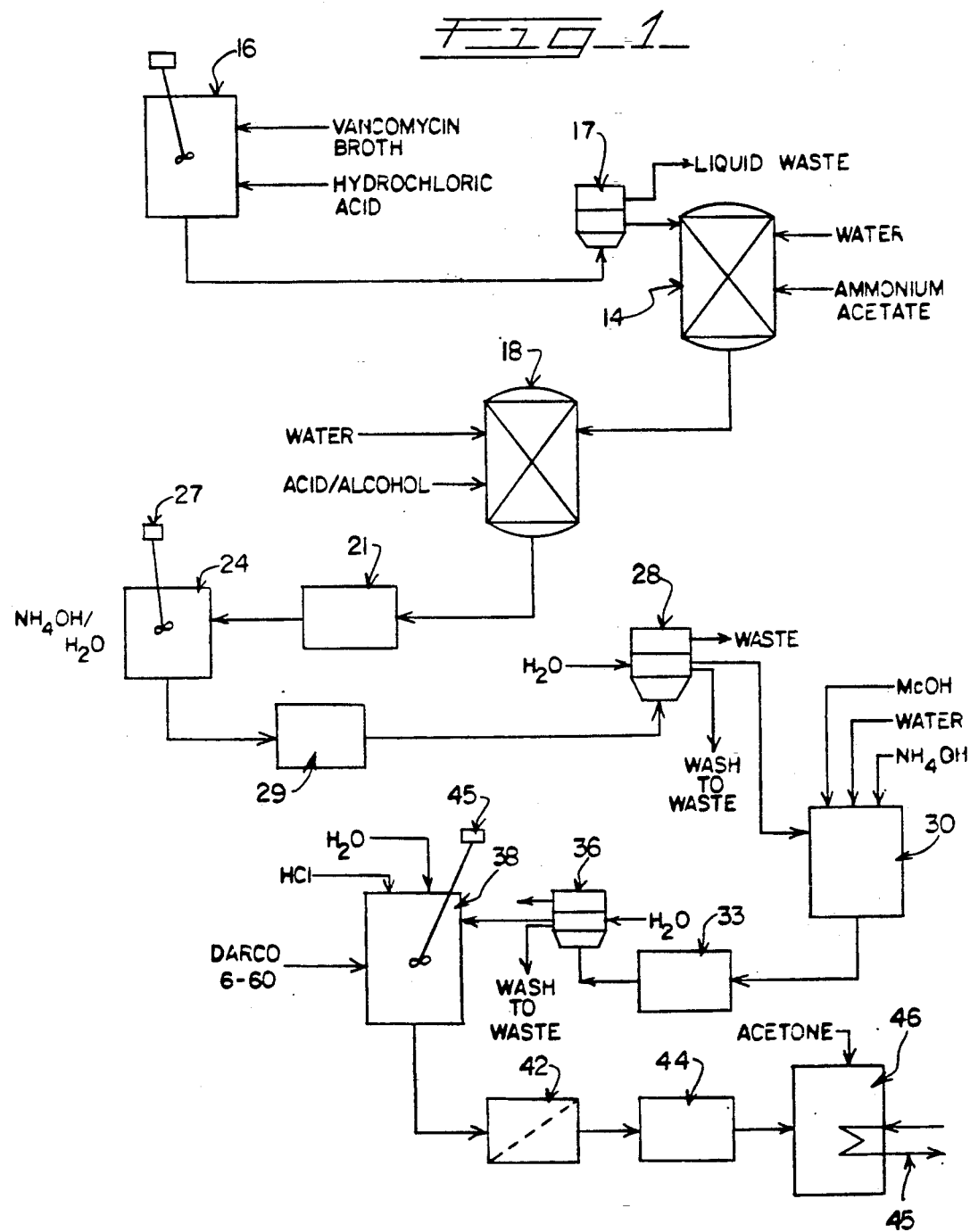

{ 5,149,784 }

PROCESS FOR MAKING VANCOMYCIN

TECHNICAL FIELD

The present invention relates to a process for the manufacture of vancomycin.

BACKGROUND OF THE INVENTION

Vancomycin is used to treat serious infections of methicillin-resistant staphylococci. Vancomycin is produced by cultivating the bacteria S. orientalis in a nutrient culture media.

The vancomycin broth is filtered and added to a column that contains an adsorption resin that decolorizes and desalts the vancomycin. The resin is washed, and the vancomycin eluted with a solvent of low pH, followed by decolorization with carbon.

The vancomycin eluant is then further purified using a single recrystallization step at low pH. The crystallized vancomycin is combined with a strong acid such as hydrochloric acid (HCl) and precipitated in an organic solvent such as acetone to form vancomycin.HCl. This process for the manufacture and purification of vancomycin HCl is disclosed in U.S. Pat. No. 3,067,099 to McCormick et al.

In another example of a prior art process for the manufacture of vancomycin.HCl, a solvent of 0.1% phosphoric acid ($H_3PO_4$) in a solution of 10% isopropyl alcohol (IPA) is used to elute purified vancomycin from the adsorption column. The vancomycin eluant is then concentrated using reverse osmosis or vacuum evaporation. An aqueous solution that contains approximately 60 g/l of potassium phosphate ($KH_2PO_4$) is added to the concentrated vancomycin solution. The $KH_2PO_4$ causes the vancomycin to crystallize from the solution. The resulting slurry is centrifuged to remove the excess liquid. The vancomycin crystals obtained from centrifugation of the slurry are reslurried in sodium hydroxide (NaOH) to a pH of approximately 4.5 followed by treatment with $KH_2PO_4$ to a pH of approximately 2.0. Vancomycin again crystallizes from the solution. The resulting slurry is centrifuged to separate the crystals from the liquid. The resultant solid is dissolved in water and the mixture is eluted in an ion-exchange column to prepare vancomycin hydrochloride.

European Patent Application, Publication No. 0323150 to Catt et al. discloses an alternate method to precipitate vancomycin in a base solution with a pH of 7.8 to 9.0. At pH's above about 9.0, the base crystallization disclosed in Catt et al. is unsatisfactory because reduced yields and discolored products result; pH's of 8.0 to 8.5 are preferred for the crystallization disclosed by this reference.

SUMMARY OF THE INVENTION

The present invention is directed to a process for the manufacture of vancomycin using base crystallization at a pH greater than 9.0. Vancomycin is concentrated and purified by elution with a base solvent that has a pH of 9.0 to 9.5 through a column with a suitable adsorbent therein followed by elution through a second column with another suitable adsorbent therein which decolorizes and desalts the vancomycin. The solvent used in the second column is an acid/alcohol solution, the alcohol being an approximately 10% solution of ethanol or isopropyl alcohol. Base is added to the vancomycin eluant in an amount sufficient to impart to the resulting solution a pH of approximately 9.5 to 10.5 followed by the addition of methanol to the solution. The methanol and ammonia are evaporated from the solution. The vancomycin crystallizes and precipitates from the solution. The crystals are then separated from the solution.

The crystals are reslurried in water. A sufficient amount of base is added to the slurry to increase the pH of the solution to about 9.5 to about 10.5 to completely dissolve vancomycin base crystals. Methanol is then added to the solution, and vancomycin crystals begin to form. After separating the resulting crystals from the solution, they are dissolved by adding hydrochloric acid in an amount sufficient to decrease the pH of the dissolved solution to about 3.0 to about 3.5. The acidified, dissolved solution is then concentrated and the crystallized vancomycin.HCl is precipitated from the solution in an organic solvent.

The present process has several advantages over the prior art. First, the vancomycin purity from this process ($90\pm1\%$) is at least 2-3% higher than those obtained by other processes. The purity is greatly increased during base crystallizations at pH 9.0-9.5 without additional chromatographic, extraction, or complex formation steps for further purification. Secondly, some time-consuming and expensive conversion steps using ion-exchange resins to obtain the desired hydrochloride salt are totally eliminated. Finally, the overall yield is higher than those of prior art processes due to the process simplification and smaller activity loss during base crystallization at pH 9.0-9.5.

BRIEF DESCRIPTION OF THE DRAWINGS

FIG. 1 is a flow diagram of an embodiment of the process disclosed herein.

DETAILED DESCRIPTION OF THE PREFERRED EMBODIMENTS

Vancomycin typically is prepared in a fermentor. Vancomycin is then separated for activity and purified. Typically, the desired vancomycin is separated from other strains of vancomycin and other impurities by elution of "raw" vancomycin through a column with an adsorbent therein. The preferred active strain of vancomycin is vancomycin B. For purposes of this disclosure, adsorbents that are selective for vancomycin B such as DOWEX 50 WX2, a cross-linked cation-exchange resin available from Dow Chemical, and AMBERLITE XAD-16, a non-functional macroriticular resin available from Rohm & Haas, are utilized to separate other strains of vancomycin and impurities from the vancomycin B.

Elutions are performed in fractions. Each fraction is analyzed to determine the concentration and quantity of vancomycin B therein. In this way the fractions with the greatest concentration of vancomycin B can be combined to optimize the yield from the process. The fractions, for convenience, are expressed in the number of bed or column volumes they represent. The purity of the vancomycin varies from fraction to fraction and depends on a number of factors such as the solvent and the fermentation medium used.

Referring to FIG. 1, a harvested vancomycin culture is mixed in tank 12 with approximately $7000\pm1000$ liters of a cation exchange resin such as DOWEX 50 WX2. The resin and culture are mixed in mixer 13 for approximately two hours. The pH of the mixture is maintained at $6.0\pm0.2$ by adding sulphuric acid or hydrochloric acid as required. The enriched resin is separated from the excess solution using a centrifuge 17.

The enriched resin is then washed in water and placed in adsorption column 14. The adsorption column 14 is eluted with a base solution of an ammonium salt such as 42,000±6,000 liters of a 0.5±0.05 M ammonium acetate solution at a pH of 9.25±0.1 or 0.25±0.05 M ammonium hydroxide solution. The flow rate of the base solution through the column is not to exceed 10,500 liters per hour.

Fractions of 2500±500 liters are collected and the pH of the fractions is adjusted to 7.5±0.5 by adding 5±2% hydrochloric acid to the fractions. The fractions are analyzed using high pressure liquid chromatography (HPLC) (not shown) for the presence and purity of vancomycin B. The vancomycin B fractions are then combined. The combined fractions from column 14 are loaded onto column 18 which is filled with a polymeric adsorption resin such as XAD-16 with a bed volume of 2300±200 liters. The XAD-16 resin is suitable for desalting and decolorizing the vancomycin. The maximum flow rate through the resin bed is 3300 liters per hour.

The resin is washed with 2300±500 liters of distilled water. The enriched resin is then eluted with 11,500±2500 liters of an acid/alcohol solvent such as, for example, 0.1%±0.05% HCl in an aqueous solution that is 10%±2% alcohol such as ethyl alcohol or isoproxy alcohol. The maximum flow rate of the solvent through the resin bed is 3500 liters per hour.

Fractions from the eluted column are collected and analyzed for the presence and purity of vancomycin B using HPLC or thin layer chromatography (TLC). The fractions are approximately 1500±500 liters apiece. The fractions with adequate activity are then combined. The eluant from column 18 is concentrated by reverse osmosis in module 21. Vacuum evaporation in an evaporator (not shown) at 25° C. (77° F.) is also effective. The vancomycin eluate is concentrated to approximately 200±50 g/l.

The concentrated solution is placed in a vessel 24 to which is added a base solution such as, for example, ammonia water (NH4OH/H2O). Sufficient base is added to raise the pH of the concentrated solution to 10.0±0.5. The solution is mixed using a mixer 27 for ten minutes until complete dissolution is achieved. An aliquot of 750±250 liters of methanol is added to the solution, and a slurry results. The methanol and ammonia are then extracted from the slurry using reverse osmosis 29. A vacuum evaporator (not shown) is also effective.

The solids are separated from the solution using a centrifuge or filter 28. The solids are washed with 750±250 liters of distilled water and are deposited in vessel 30 where they are reslurried in 750 ±250 liters of water followed by adding a base, such as NH4OH, to vessel 30 in an amount sufficient to raise the pH to 10.0±0.5. The filtrate is discarded.

An aliquot of 750±250 liters of methanol is added to the solution. A precipitate results. The methanol and ammonia are removed from the solution using reverse osmosis in module 33. In an alternate embodiment, module 33 can also be a vacuum evaporator. The precipitate is separated from the solution in a centrifuge or filter 36. The retentate from the centrifuge or filter 36 is washed with 750±250 liters of distilled water or a mixture of methanol, acetone, and distilled water.

The washed retentate (vancomycin base) is placed in vessel 38. Water, in an amount of 750±250 liters, is added to vessel 38 to reslurry the solid precipitate. Hydrochloric acid is added in an aliquot sufficient to decrease the slurry pH to 3.25±0.25 and to dissolve the solid in solution.

Approximately 8±4 kilograms of DARCO G-60 activated carbon manufactured by ICI, is added to the solution. The mixture is then stirred for an hour using mixer 45 and the mixture is filtered through filter 42 which contains 0.3 µ and 0.1 µ filter cartridges. The filtered solution is concentrated using reverse osmosis module 44 to a solid content of 250±25 g/l. The concentrated solution is placed in tank 46 to which 2400±600 liters of acetone is added. The mixture is then chilled to less than 7° C. (44.6° F.) using cooler 45 and a solid product precipitates therefrom.

EXAMPLE I

Analysis of Product Made by The Disclosed Process

A crystallized vancomycin.HCl product was made according to the above process and analyzed for purity, biopotency and other properties to determine the acceptability of the product. Table I summarizes the results of these analyses.

TABLE I

ANALYSIS OF PRODUCT MANUFACTURED BY THE PREFERRED EMBODIMENT OF THE PROCESS

|  | CODE SPECIFICATIONS | PRODUCT ANALYSIS |
|---|---|---|
| Biopotency (anhydrous) | ≧925 µg/mg | 1116 µg/mg |
| Appearance | powder | acceptable |
| Color | white to light tan | acceptable |
| pH | 2.8–4.2 | 3.85 |
| % Moisture | ≦4.0% (w/w) | 3.66% |
| Identification (by IR) | USP | acceptable |
| Identification (by HPLC) | standard retention time | acceptable |
| Vancomycin B (by HPLC) | ≧83.0% | 92.9% |
| Largest Single Impurity (by HPLC) | <5.0% | 1.4% |
| Pyrogen | standard | acceptable |

EXAMPLE II

Analysis of Vancomycin Purified By A MeOH/NH4OH Recrystallization

Table II is a summary of product analyses performed on vancomycin purified by MOH/NH4OH crystallizations as described in the foregoing procedure. Table II illustrates that a product of acceptable purity and activity is produced by the process herein described while providing overall yields of 68 to 80 percent.

TABLE II

| Preparations | Product Quality[1] and Yield from MeOH/NH4OH Crystallizations | | | | | |
| | 1 | 2 | 3 | 4 | 5 | 6 |
|---|---|---|---|---|---|---|
| Start material | Vanco.HCl (400 APHA) | Van.HCl (400 APHA) | 2nd Crop | XAD-16 Conc. | XAD-16 Conc. | XAD-16 Conc. |
| HPLC[2] Purity | 91.2% | 89.6% | 90.0% | 91.6% | 92.9% | 90.1% |
| LSI[3] impurity | 1.7% | 1.7% | 1.7% | 1.5% | 1.4% | 1.9% |

TABLE II-continued

Product Quality[1] and Yield from MeOH/NH4OH Crystallizations

| Preparations | 1 | 2 | 3 | 4 | 5 | 6 |
|---|---|---|---|---|---|---|
| APHA[4] Color | 100 | 200 | 250 | 200 | 150 | 200 |
| pH | 3.6 | 4.0 | 3.7 | 3.1 | 3.9 | 2.6 |
| % Moisture | 2.6% | 0.6% | 1.9% | 2.8% | 3.7% | 2.8% |
| % ROI (residue on ignition) | 0.0% | 0.0% | 0.0% | 0.0% | 0.1% | 0.0% |
| % acetone | 1.8% | 0.3% | 0.2% | 0.4% | 0.7% | 0.1% |
| Heavy metal (as Pb) | <30 ppm | <30 ppm | <30 ppm | <30 ppm | <30 ppm | <30 ppm |
| BioPotency (μg/mg) | 1066 | 1089 | 1077 | 1060 | 1116 | 1093 |
| % NH4 | 0.07% | 0.09% | 0.05% | 0.09% | 0.9 | 0.1% |
| % Cl | 2.7% | 2.7% | 2.7% | 2.9% | 2.5% | 3.0% |
| % PO4 | ND | ND | ND | ND | ND | ND |
| % SO4 | ND | ND | ND | ND | ND | ND |
| Yields (NH4Cl Cxx + MeOH ReCx): | | | | | | |
| Conc- >HCl (KgA) | 68% | 74% | 78% | 80% | 70% | 80% |
| (KgW) | 75% | 83% | 87% | 87% | 75% | 89% |
| Overall (KgW) assume 90% beer absorption | 68% | 75% | 78% | 78% | 68% | 80% |

Notes
[1] All products were in powder form and met color requirements, as well as infrared identification.
[2] High Pressure Liquid Chromatography
[3] Largest single impurity
[4] APHA (American Public Health Association)

The foregoing process description and example are intended as illustrations only and not intended to limit the invention in any way except in the spirit and scope of the appended claims.

We claim:

1. A process for the manufacture of vancomycin comprising:
   a) exposing a vancomycin-containing culture to a first adsorbent and eluting the vancomycin from said first adsorbent with a solvent selected from the group consisting of solutions of ammonium hydroxide and ammonium salts;
   b) passing the vancomycin eluate produced by step a) through a second adsorbent;
   c) adding a solution of base to the product of step b) to produce a solution with a pH of about 9.5 to about 10.5;
   d) adding methanol to the solution of step c) thereby crystallizing the vancomycin from the solution;
   e) substantially separating the crystals from the solution;
   f) slurrying the crystallized vancomycin from step e);
   g) adding to the product of step f) a base solution in an amount sufficient to increase the pH of the resulting solution to about 9.5 to about 10.5;
   h) adding methanol to the solution of step g) thereby recrystallizing vancomycin from the solution; and
   i) substantially separating the crystals from the solution.

2. The process of claim 1 further comprising:
   a) titrating the recrystallized vancomycin from step i) with hydrochloric acid to obtain a vancomycin solution with a pH of about 3.0 to about 3.5; and
   b) precipitating vancomycin HCl from the solution.

3. A process according to claim 1 wherein the ammonium salt is ammonium acetate.

4. The process of claim 1 further comprising the step of eluting the vancomycin eluate of step b) with an acid/alcohol solution.

5. The process of claim 1 further comprising the step of concentrating the product from step b).

6. The process of claim 1 further comprising the step of extracting the methanol and the base from at least one of the solutions of step d) and h).

7. The process of claim 6 wherein the base and methanol are extracted by reverse osmosis.

8. The process of claim 6 wherein the base and methanol are extracted by vacuum evaporation.

9. The process of claim 1 wherein the crystals in step f) are slurried in distilled water.

10. The process of claim 2 wherein the vacomycin.HCl in step b) is precipitated in acetone.

11. A process for the manufacture of vancomycin in which a vancomycin broth is passed through first and second adsorbents wherein the improvement comprises:
   a) adding a solution of base to the adsorbed broth to produce a solution with a pH of about 9.5 to about 10.5;
   b) adding methanol to the solution of step a) thereby crystallizing the vancomycin from the solution;
   c) adding to the crystallized vancomycin a base solution in an amount sufficient to increase the pH of the resulting solution to about 9.5 to about 10.5; and
   d) adding methanol to the solution of step c) thereby recrystallizing vancomycin from the solution.

* * * * *